(12) United States Patent
Ho (10) Patent No.: US 11,448,382 B1
(45) Date of Patent: Sep. 20, 2022

(54) SANITIZER DEVICE

(71) Applicant: OXTI CORPORATION, New Taipei (TW)

(72) Inventor: Chih-Feng Ho, New Taipei (TW)

(73) Assignee: OXTI CORPORATION, New Taipei (TW)

( * ) Notice: Subject to any disclaimer, the term of this patent is extended or adjusted under 35 U.S.C. 154(b) by 0 days.

(21) Appl. No.: 17/232,152

(22) Filed: Apr. 16, 2021

(51) Int. Cl.
  *F21V 17/10* (2006.01)
  *F21V 15/01* (2006.01)
  *A61L 9/20* (2006.01)

(52) U.S. Cl.
  CPC ............... *F21V 17/10* (2013.01); *A61L 9/20* (2013.01); *F21V 15/01* (2013.01); *A61L 2209/15* (2013.01)

(58) Field of Classification Search
  None
  See application file for complete search history.

(56) References Cited

U.S. PATENT DOCUMENTS 10,894,104 B1 * 1/2021 Kim .......................... A61L 2/10

FOREIGN PATENT DOCUMENTS

CN 108294721 A * 7/2018
CN 111720015 A * 9/2020

* cited by examiner

*Primary Examiner* — Andrew Smyth
(74) *Attorney, Agent, or Firm* — Leong C. Lei (57) ABSTRACT

The sanitizer device includes a main member, a sanitizing lamp, a clamp member, and a fastening member. The sanitizing lamp, inside the main member, includes a lighting element, a sensor element, a control element, and a power element. The clamp member is configured to an end of the main member, and includes two symmetrical and oppositely positioned clamps. The clamps form a close space when moved towards each other and joined together. The clamps respectively have a through openings, and the fastening member runs through the through openings to tie the clamps together. To mount the sanitizer device onto a door handle, the clamps are closed around the door handle. The sanitizing lamp emits disinfecting light on door handle to sanitize the door handle. When the sensor element detects an object in the proximity, the sensor element notifies the control element to turn off the sanitizing lamp.

5 Claims, 9 Drawing Sheets

SANITIZER DEVICE

BACKGROUND OF THE INVENTION

(a) Technical Field of the Invention

The present invention is generally related to sanitizer devices, and more particular to a sanitizer device for door handle.

(b) Description of the Prior Art

Infectious diseases are one of the main causes to the death of world population. Due to life-style and climate changes, viruses and pathogenic microorganisms continuously evolve and various emerging infectious diseases and re-emerging infectious diseases have increased significantly. From measles, smallpox, malaria, flu, to recent SARS, H1N1, MERS-CoV, and COVID-19, these infectious diseases are spread mainly through direct contact with secretions or droplets with virus.

Door handles are a common route for virus transmission. Therefore, China Utility Model Patent No. CN211751244U teaches an automated sanitizer device for door handles where a container of disinfectant is attached to a door handle by electromagnet. The disinfectant is sprayed to the door handle through a nozzle.

However, disinfectant is corrosive and irritating to skin, in addition to stimulating odor. The amount of disinfectant limits how many times the disinfectant may be applied and, in prolonged the operational time, a large capacity for the disinfectant is required, which implies bulky size. Furthermore, the device adheres to the door handle through electromagnet, meaning that the door handle has to have a metallic panel.

SUMMARY OF THE INVENTION

The present invention therefore teaches a novel sanitizer device for sanitizing a door handle. The sanitizer device includes a main member, a sanitizing lamp, a clamp member, and a fastening member. The sanitizing lamp, inside the main member, includes a lighting element, a sensor element, a control element, and a power element. The clamp member is configured to an end of the main member, and includes two symmetrical and oppositely positioned clamps. At least one of the clamps is pivotally connected to the main member through a pin. The clamps form a close space when moved towards each other and joined together. The clamps respectively have a through openings, and the fastening member runs through the through openings to tie the clamps together.

Preferably, the clamps respectively include a half ring, and a close space is formed when the half rings joined together.

Preferably, the clamp member includes a power chamber.

Preferably, the sanitizing lamp includes a reception element which is a wireless signal receiver.

Preferably, the main member has a semi-cylindrical outer surface that is convex outward and a semi-cylindrical inner surface that is concave inward.

To mount the sanitizer device onto a door handle, the clamps are opened and then closed around the door handle. The sanitizing lamp emits disinfecting light on door handle to sanitize the door handle. When the sensor element detects an object appearing in the proximity of the door handle, such as a human hand, the sensor element notifies the control element, and the control element turns off the sanitizing lamp so that the human hand would not be harmed. The main member also has a power chamber to accommodate the power element, and the sanitizing lamp may further include a reception element to receive a wireless signal. The control element, based on the wireless signal, turns on or off the lighting element.

The foregoing objectives and summary provide only a brief introduction to the present invention. To fully appreciate these and other objects of the present invention as well as the invention itself, all of which will become apparent to those skilled in the art. The following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather. The following description provides a convenient illustration for implementing exemplary embodiments of the invention. Various changes to the described embodiments may be made in the function and arrangement of the elements described without departing from the scope of the invention as set forth in the appended claims.

Figure 1:
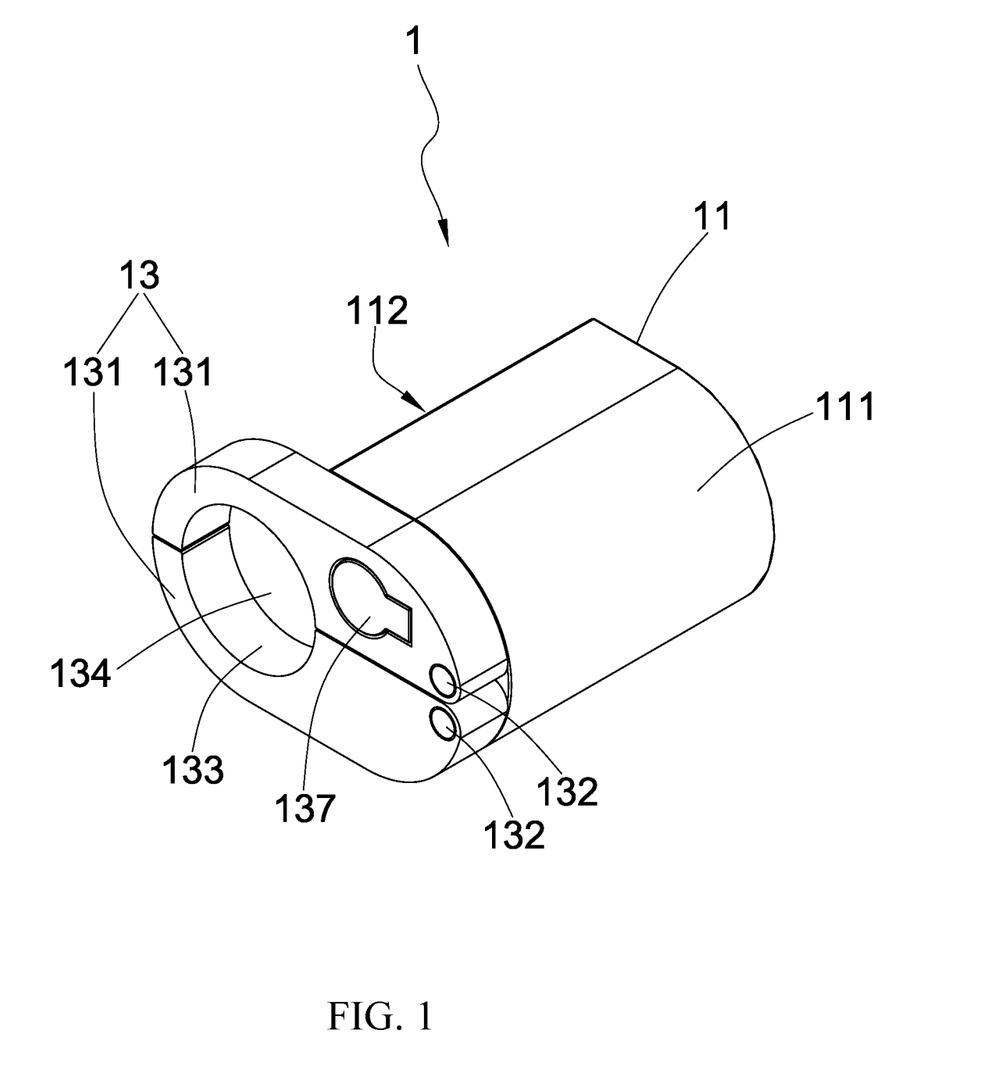
FIG. 1 is a perspective diagram showing a sanitizer device according to an embodiment of the present invention.
Figure 4:
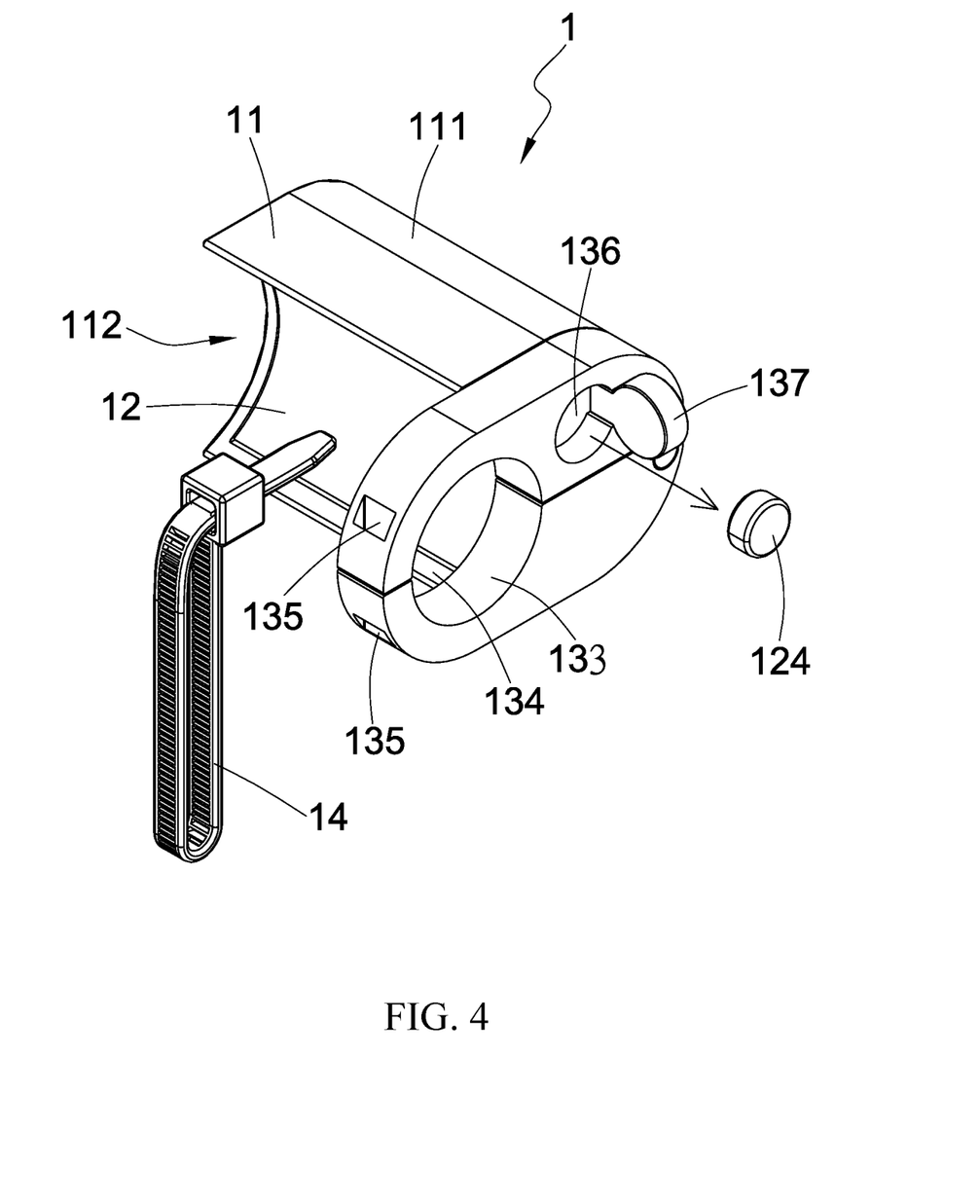
FIG. 4 is a perspective diagram showing the power chamber of the sanitizer device of FIG. 1.

As shown in FIG. 1, a sanitizer device 1 according to an embodiment of the present invention includes a main member 11, a sanitizing lamp 12, a clamp member 13, and a fastening member 14 (see FIG. 4).

The main member 11 has a semi-cylindrical outer surface 111 that is convex outward and a semi-cylindrical inner surface 112 that is concave inward. The two surfaces, without sharp angles, prevent cut to users.

Figure 3:
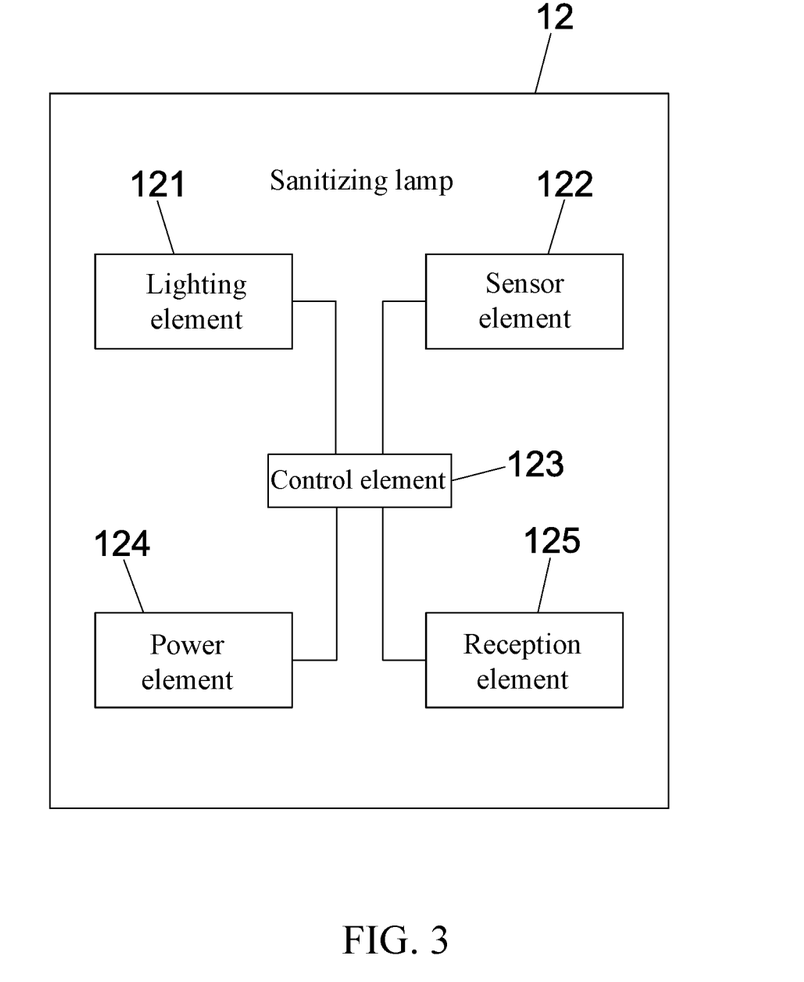
FIG. 3 is a functional block diagram showing the sanitizing lamp of the sanitizer device of FIG. 1.

As shown in FIG. 3, the sanitizing lamp 12 is disposed inside the main member 11 and exposed from the inner surface 112. The sanitizing lamp 12 includes a lighting element 121, a sensor element 122, a control element 123, a power element 124, and a reception element 125. The sanitizing lamp 12 emits disinfecting light such as ultraviolet (UV) light for sanitization. The lighting element 121 is the light source of the sanitizing lamp 12. The lighting element 121 may be a UVB lamp, a UVC lamp, a mercury-vapor lamp, a metal halide lamp, or a xenon lamp, but is not limited as such. The sensor element 122 detects the proximity of an object such as a human hand 3 (see FIG. 9). The sensor element 122 may be an infrared sensor element, light sensor element, ultrasound sensor element, or thermal sensor element. The control element 123 turns on or off the lighting element 121. The power element 124 provides electricity to the other components such as a battery. The reception element 125 receives a wireless signal. The reception element 125 may be a wireless signal receiver, and the control element 123, based on the received wireless signal, turns on or off the lighting element 121. The wireless signal may be transmitted from a smart phone or a remote controller to the reception element 125.

Figure 2:
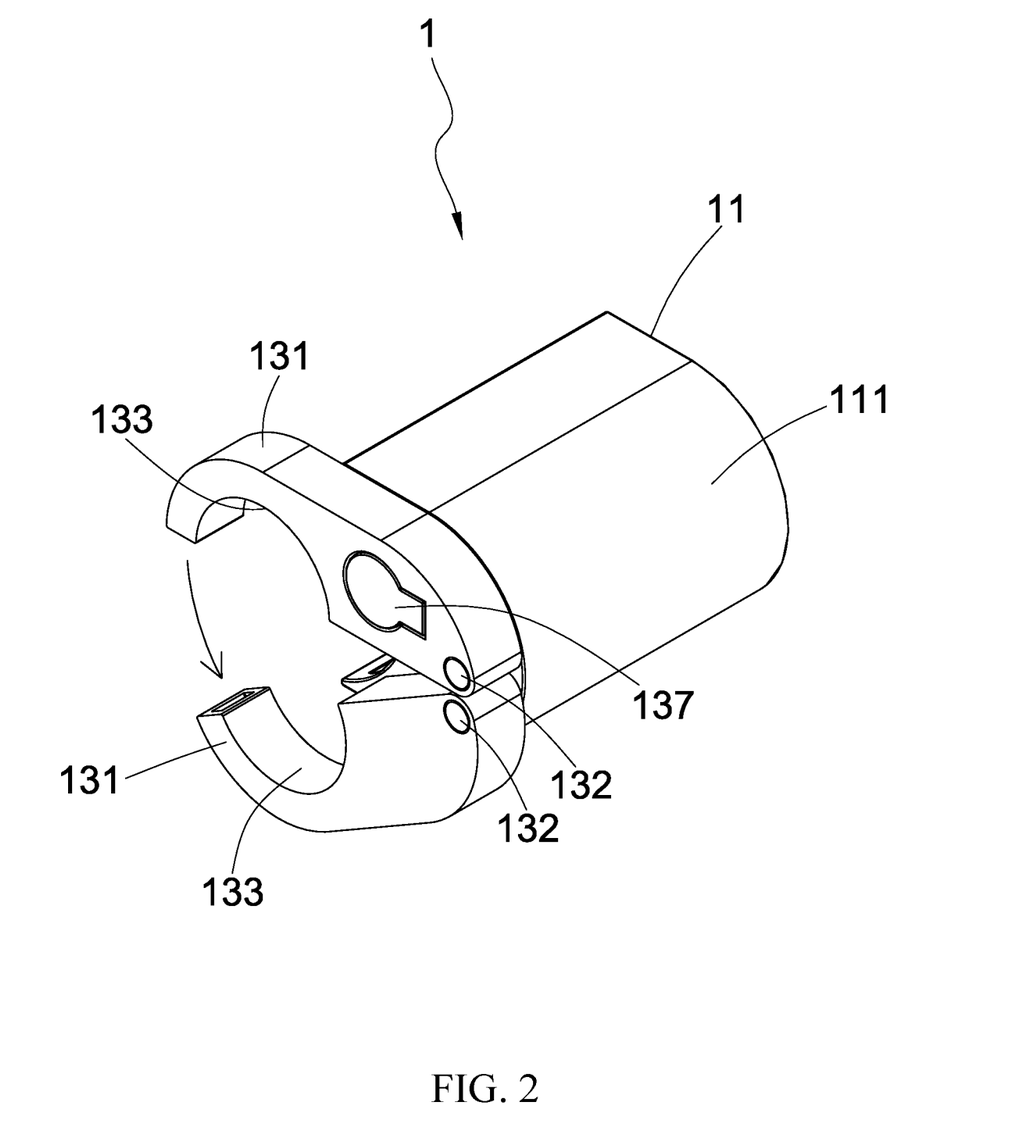
FIG. 2 is a perspective diagram showing the sanitizer device of FIG. 1 with the clamp member opened.

As shown in FIG. 2 and FIG. 3. The clamp member 13 is configured to an end of the main member 11. The clamp member 13 includes two symmetrical and oppositely positioned clamps 131. At least one of the two clamps 131 has an inner end pivotally joined to the main member 1 through a pin 132 and may pivot around the pin 132. Both clamps 131 have a half ring 133 adjacent to their outer ends. When the clamps 131 are moved toward each other, the clamps 131 has their outer ends joined together and their half rings 133 form a close space 134. Both clamps 131 also respectively have a through openings 135 through the half rings 133. The clamp member 13 may further include a power chamber 136 (see FIG. 4). The power element 124 (see FIG. 4) of the sanitizing lamp 12 may be housed in the power chamber 136. The power chamber 136 may be sealed by a protection cap 137.

Figure 7:
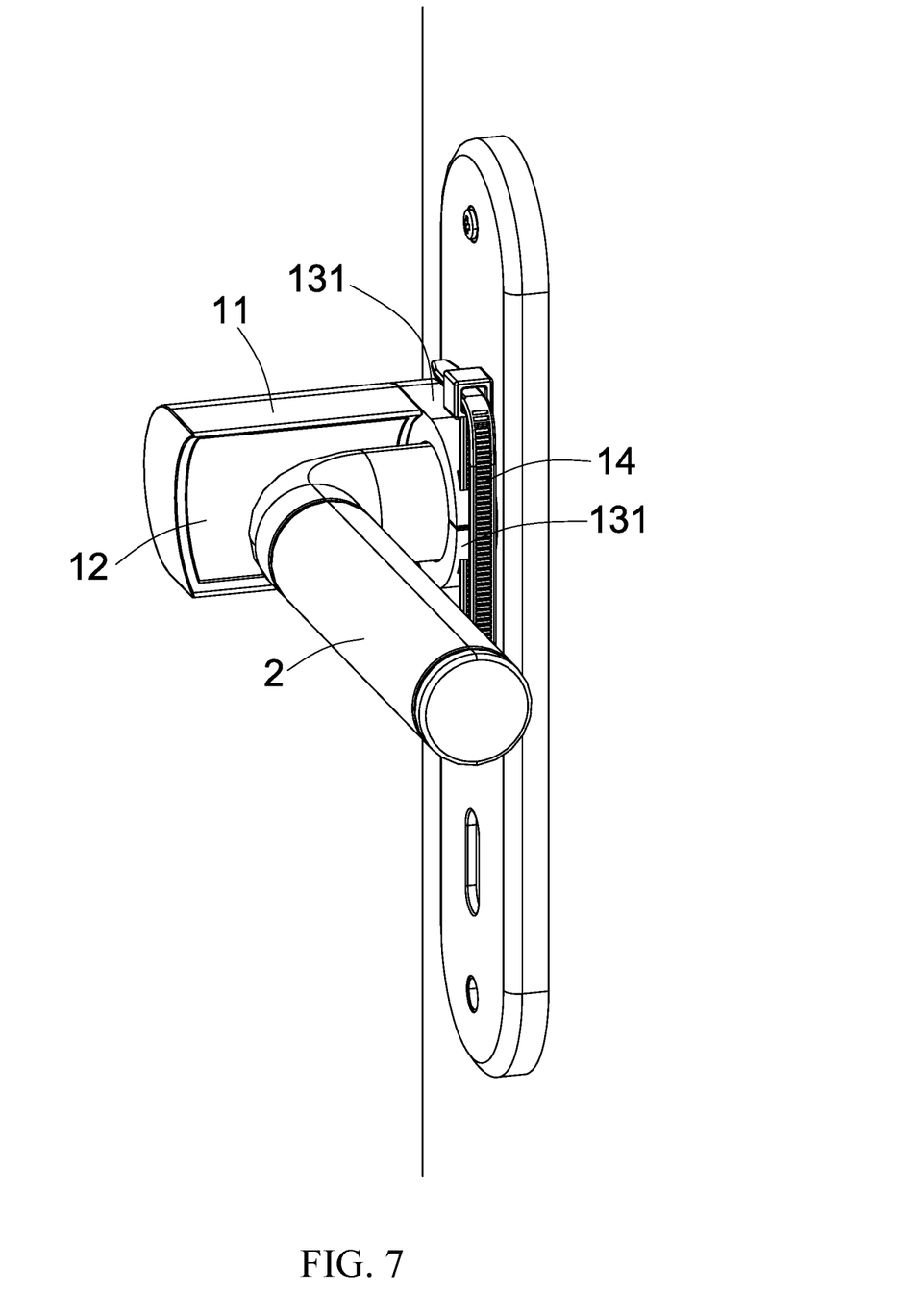
FIG. 7 is a perspective diagram showing the sanitizer device of FIG. 1 whose clamps are tied by the fastening member.

As shown in FIG. 4 and FIG. 7. The fastening member 14 is threaded through the through openings 135 of the clamps 131 so as to tie the clamps 131 together.

Figure 5:
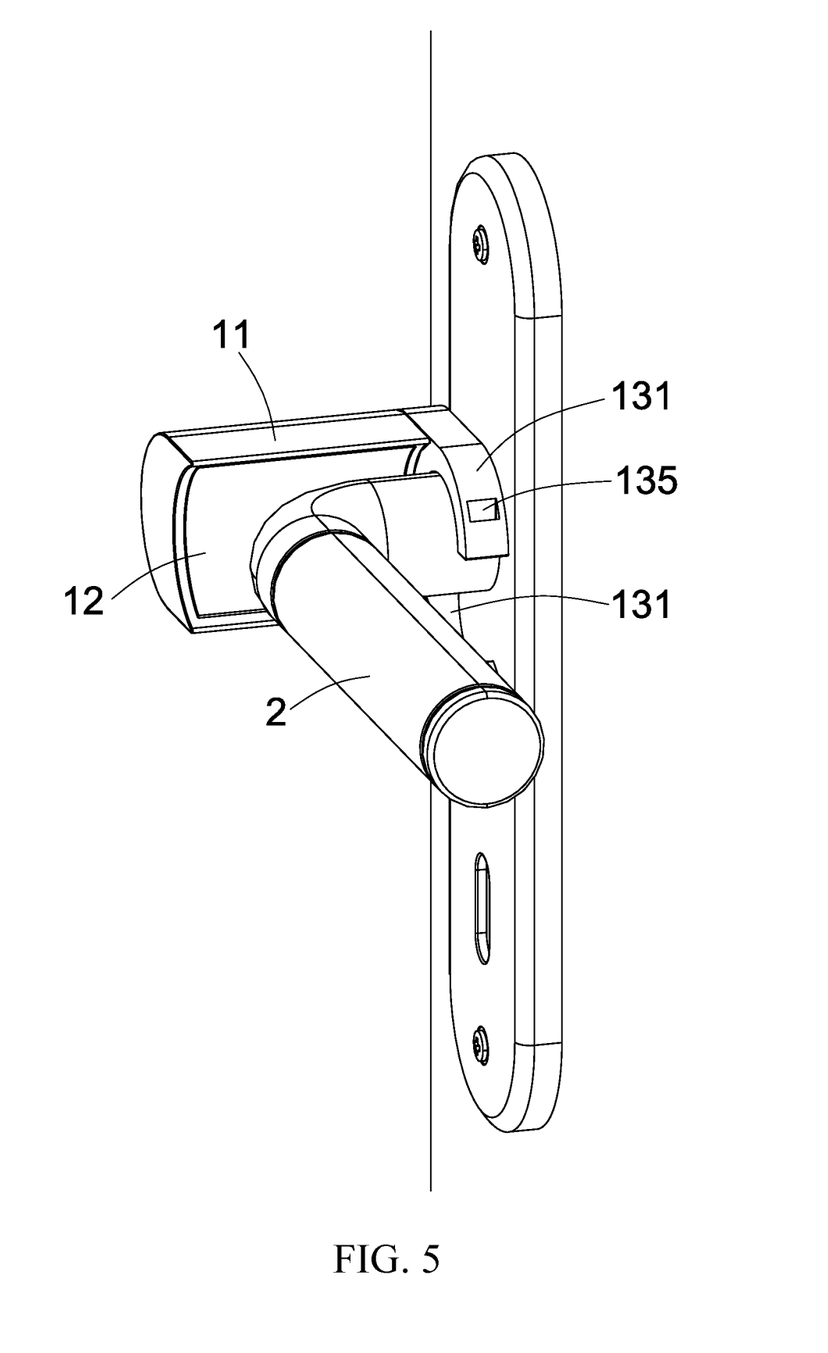
FIG. 5 is a perspective diagram showing the sanitizer device of FIG. 1 in the process of mounting onto a door handle.
Figure 6:
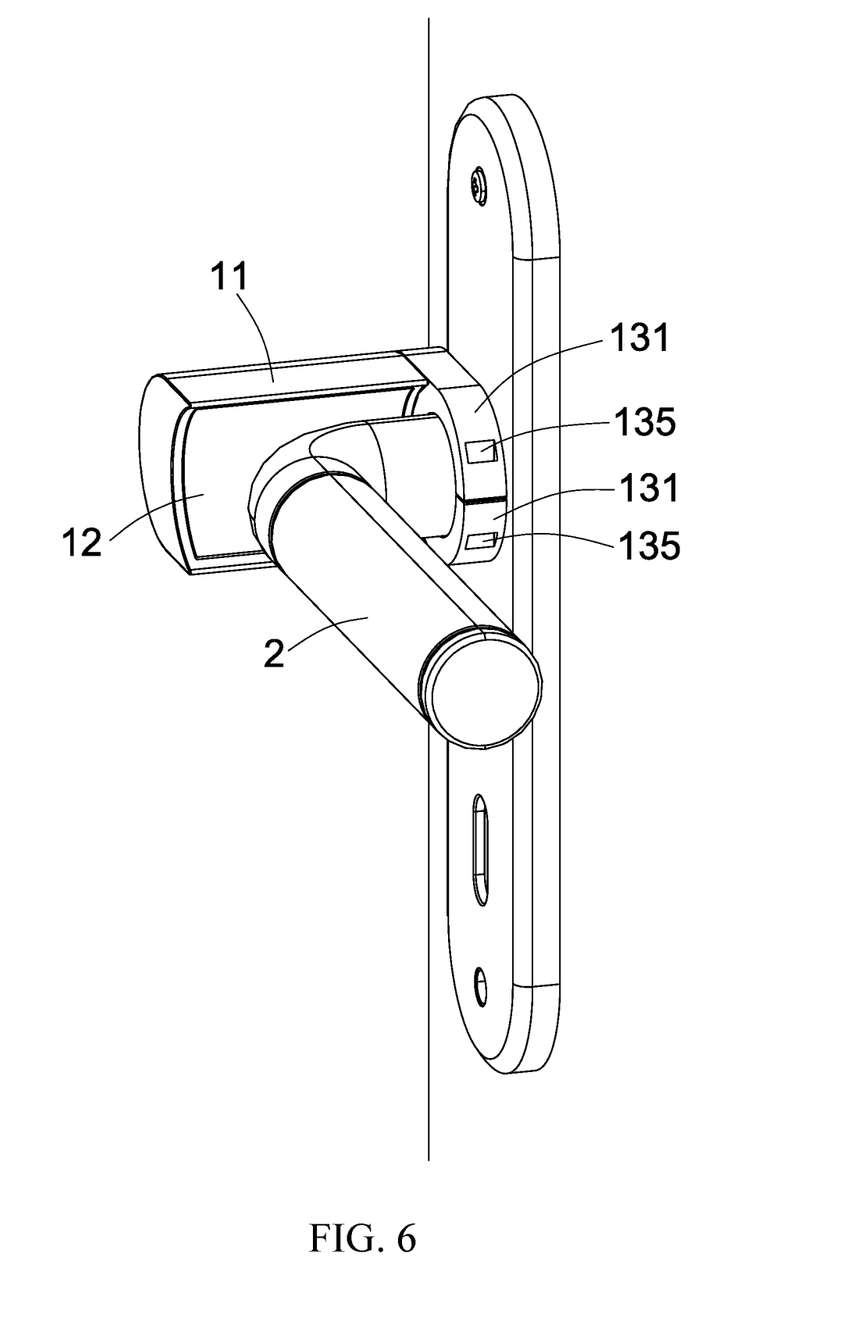
FIG. 6 is a perspective diagram showing the sanitizer device of FIG. 1 after it is mounted onto a door handle.
Figure 8:
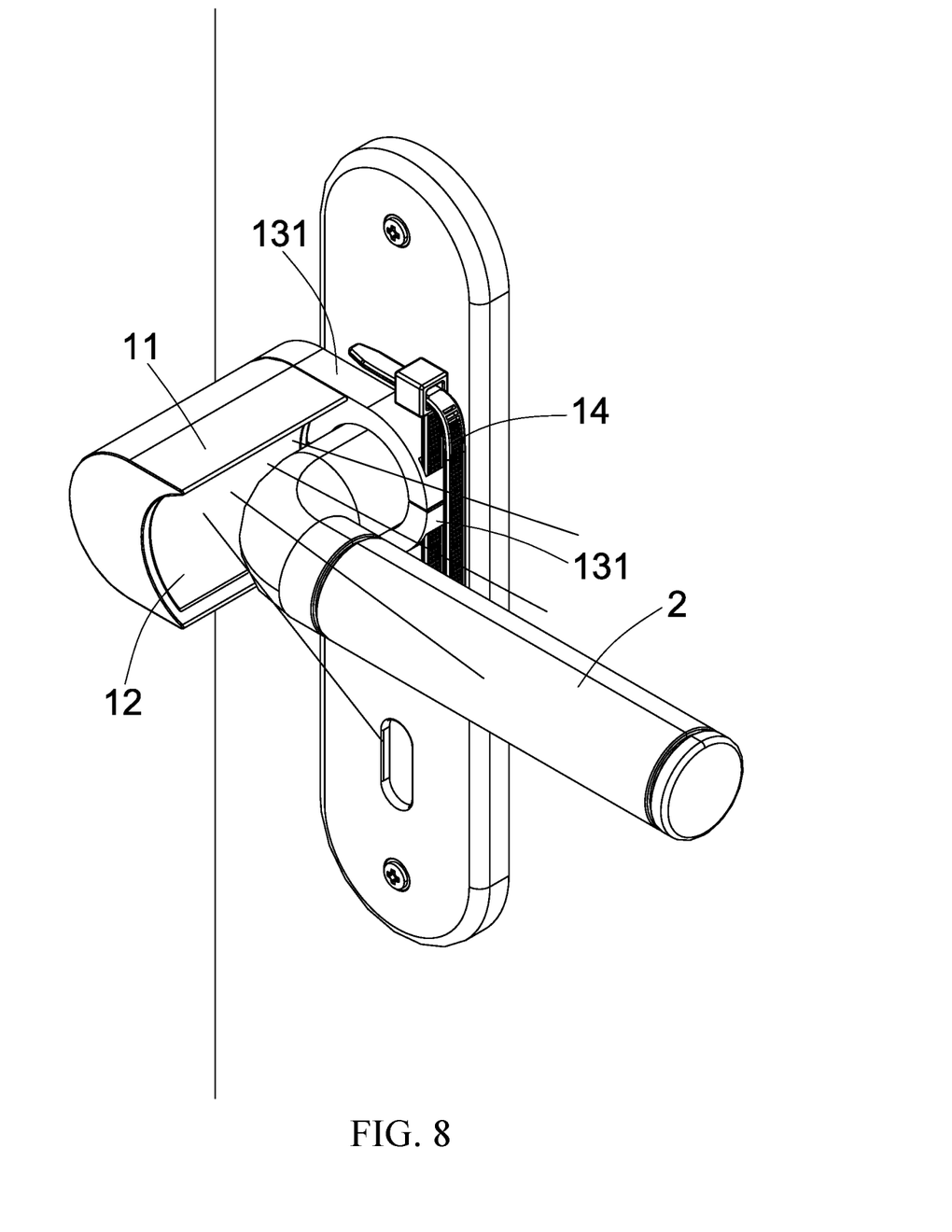
FIG. 8 is a schematic diagram showing the sanitizing lamp emits a disinfecting light on the door handle.
Figure 9:
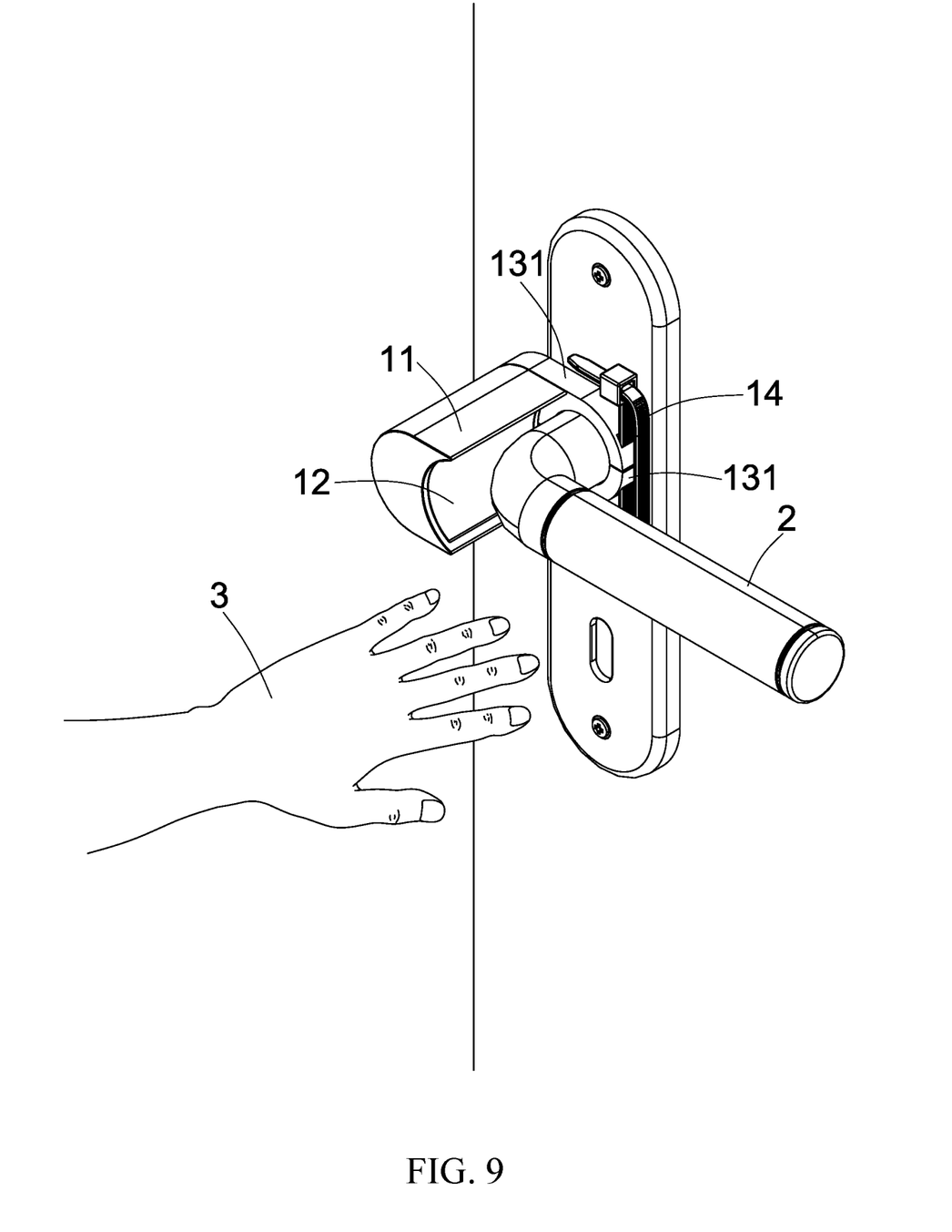
FIG. 9 is a schematic diagram showing the sanitizing lamp is turned off when a human hand is detected.

As shown in FIG. 5 and FIG. 6, to mount the sanitizer device onto a door handle 2, the clamps 131 are opened and then closed around the door handle 2. As shown in FIG. 4 and FIG. 7, the clamps 131 are then fixed together by running the fastening member 14 through the through openings 135. As shown in FIG. 8, the sanitizing lamp 12 may be remotely controlled to emit disinfecting light on door handle 2 to sanitize the door handle 2. As shown in FIG. 3 and FIG. 9, when the sensor element 122 detects an object appearing in the proximity of the door handle 2, such as a human hand 3, the sensor element 122 notifies the control element 123, and the control element 123 turns off the sanitizing lamp 12 so that the human hand 3 would not be harmed.

As described, the sanitizer device 1 may be quickly and conveniently mounted onto a door handle 2. In contrast to the prior arts, the sanitizer device is smaller in dimension and takes up little space. Its installation and removal may be easily achieved by first removing the fastening member 14 and then releasing the clamp by the clamp member 13. The fastening member 14 may be a plastic cable tie and can be easily removed by cutting it open using scissors. The sanitizing effect by UV light is superior than disinfectant. Furthermore, the mounting of the main member 11 to the door handle 2 is through the dynamic open and close of the clamps 131, instead of using electromagnetic means such as those by the prior arts. The sanitizer device of the present invention is therefore applicable to all kinds of door handles.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A sanitizer device, comprising:
   a main member;
   a sanitizing lamp inside the main member, comprising a lighting element, a sensor element, a control element, and a power element;
   a clamp member configured to an end of the main member comprising two symmetrical and oppositely positioned clamps, where at least one of the clamps is pivotally connected to the main member through a pin; the clamps form a close space when moved towards each other and joined together; and the clamps respectively have a through openings; and
   a fastening member running through the through openings to tie the clamps together.

2. The sanitizer device according to claim 1, wherein the clamps respectively comprise a half ring; and a close space is formed when the half rings joined together.

3. The sanitizer device according to claim 1, wherein the clamp member further comprises a power chamber.

4. The sanitizer device according to claim 1, wherein the sanitizing lamp further comprises a reception element, which is a wireless signal receiver.

5. The sanitizer device according to claim 1, wherein the main member has a semi-cylindrical outer surface that is convex outward and a semi-cylindrical inner surface that is concave inward.

* * * * *